United States Patent [19]

Collins et al.

[11] Patent Number: 5,177,251

[45] Date of Patent: Jan. 5, 1993

[54] HALOGENATED TETRAENYL PROSTAGLANDIN DERIVATIVES

[75] Inventors: Paul W. Collins, Deerfield; Steven W. Kramer, Evanston; Robert L. Shone, Palatine, all of Ill.

[73] Assignee: G. D. Searle & Co., Chicago, Ill.

[21] Appl. No.: 814,750

[22] Filed: Dec. 24, 1991

[51] Int. Cl.$^5$ .............................................. C07L 177/0
[52] U.S. Cl. ................................... 560/118; 560/121; 562/500; 562/503
[58] Field of Search ................ 560/118, 121; 562/500, 562/503

[56] References Cited

U.S. PATENT DOCUMENTS

| | | | |
|---|---|---|---|
| 4,499,296 | 2/1985 | Collins | 560/118 |
| 4,683,328 | 7/1987 | Collins | 560/118 |
| 5,089,524 | 2/1992 | Collins | 514/530 |

OTHER PUBLICATIONS

Chen et al., J. Org. Chem., Prostaglandins and Congeners, Synthesis of etc., 45, 2278-2282, Nov. 1979.
Collins et al., J. Med. Chem., Synthesis and Gastrointestinal Pharmacology of etc., 30, 1952-1955, Mar. 1987.

Primary Examiner—Robert Gerstl
Attorney, Agent, or Firm—Roger A. Williams; Paul D. Matukaitis

[57] ABSTRACT

The present invention relates to a novel class of halogenated tetraenyl prostaglandin compounds represented by the following general formula

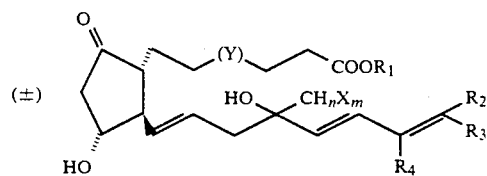

or a pharmaceutically acceptable salt thereof, wherein
Y is —CH=CH— or —CH$_2$—CH$_2$—;
R$_1$ is H or a lower alkyl of 1 to 6 carbons;
n is an integer from 0 to 3;
m is an integer from 0 to 3 and n+m=3; X is Cl or F provided that when X is Cl, n is 2 and m is 1;
R$_2$ and R$_3$ are independently H, lower alkyl from 1 to 6 carbons, Cl, —CH$_2$Cl, —CH$_2$F, —CHCl$_2$, —CCl$_3$, or taken together form a cycloalkyl of 3 to 6 carbons;
R$_4$ is H, lower alkyl from 1 to 6 carbons, Cl, F or taken together with R$_3$ form a cycloalkenyl of 4 to 6 carbons; and provided that at least one of —CH$_n$X$_m$, R$_2$, R$_3$ and R$_4$ includes a chlorine or fluorine atom.

24 Claims, No Drawings

HALOGENATED TETRAENYL PROSTAGLANDIN DERIVATIVES

BACKGROUND OF THE INVENTION

U.S. Pat. No. 4,683,328 generally describes compounds of the formula.

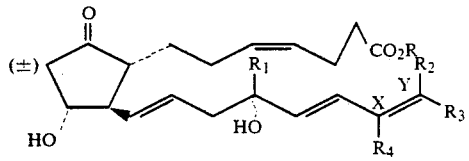

Wherein R represents hydrogen, or lower alkenyl having 1 to 6 carbon atoms; $R_1$ represents hydrogen, vinyl, or lower alkyl having 1 to 4 carbon atoms and the wavy line represents R or S stereochemistry; $R_2$, $R_3$, and $R_4$ are hydrogen or lower alkyl having 1-4 carbon atoms or $R_2$ and $R_3$ together with carbon Y form a cycloalkenyl having 4-6 carbon atoms, or $R_3$ or $R_4$ together with carbons X and Y form a cycloalkenyl having 4 to 6 carbons. The compounds are disclosed as having cytoprotective activity and gastric antisecretory activity and can be useful in the inhibition of stomach lesions such as ulcers. The patent teaches that the compounds have a lower diarrhea side effect than other prostaglandin analogs commonly associated with antisecretory/cytoprotective activity.

While the tetraenyl compounds have exhibited good cytoprotective and antisecretory activities while minimizing the diarrheal side effect commonly associated with prostaglandin analogs, the tetraenyl compounds also exhibit a stability concern that lessens the importance of the compounds as potential commercial candidates for the treatment of stomach lesions or gastrointestinal lesions such as ulcers. Specifically, these compounds readily undergo allylic rearrangement and dehydration degration reactions under acidic conditions (see Collins, et al., *J. Med. Chem.* 33, 2784, (1990)).

It would be desirable to provide compounds which exhibit protective activity while exhibiting a stability profile that would make the compounds beneficial for the treatment of animals experiencing gastrointestinal lesions and in need of cytoprotective therapy. It would also be desirable that such compounds maintain the lessened diarrheal side effect such as that exhibited with the compounds disclosed in the above noted patent reference.

SUMMARY OF THE INVENTION

The present invention relates to a novel class of halogenated tetraenyl prostaglandin compounds represented by the following general formula

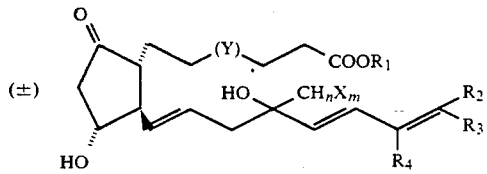

or a pharmaceutically acceptable salt thereof, wherein
Y is —CH=CH— or —CH$_2$—CH$_2$—;
$R_1$ is H or a lower alkyl of 1 to 6 carbons;
n is an integer from 0 to 3;
m is an integer from 0 to 3 and n+m=3;
X is Cl or F provided that when X is Cl, n is 2 and m is 1;
$R_2$ and $R_3$ are independently H, lower alkyl from 1 to 6 carbons, Cl, —CH$_2$Cl, —CH$_2$F, —CHCl$_2$, CHF$_2$, —CCl$_3$, —CF$_3$ or taken together form a cycloalkyl of 3 to 6 carbons; $R_4$ is H, lower alkyl from 1 to 6 carbons, Cl, F or taken together with $R_3$ form a cycloalkenyl of 4 to 6 carbons; and provided that at least one of —CH$_n$X$_m$, $R_2$, $R_3$ and $R_4$ includes a chlorine or fluorine atom.

More specifically, the invention herein is directed to a halogenated tetraenyl compound of the formula

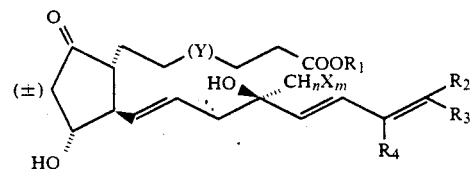

or a pharmaceutically acceptable salt thereof, wherein
Y is —CH=CH— or —CH$_2$—CH$_2$—;
$R_1$ is H or a lower alkyl of 1 to 6 carbons;
n is an integer from 0 to 3;
m is an integer from 0 to 3 and n+m=3;
X is Cl or F provided that n is 2 and m is 1 when X is Cl;
$R_2$ and $R_3$ are H, lower alkyl from 1 to 6 carbons, —CF$_3$, Cl or taken together form a cycloalkyl of 3 to 6 carbons;
$R_4$ is H, lower alkyl from 1 to 6 carbons, F or taken together with $R_3$ form a cycloalkenyl of 4 to 6 carbons; and provided that at least one of —CH$_n$X$_m$, $R_2$, $R_3$ and $R_4$ includes a chlorine or a fluorine atom.

The invention further relates to pharmaceutical compositions including a compound of formula I or II above and a pharmaceutically acceptable carrier. Such compounds and compositions have shown cytoprotective activity and gastric antisecretory activity with low diarrheagenic side effects. The compounds and the compositions can be useful in the treatment of disorders arising as a result of gastric secretion or which can be treated by the cytoprotective activity offered by the compounds and compositions, such as gastrointestinal ulcers and lesions which can be induced by nonsteroidal anti-inflammatory drugs, alcohol and the like.

DETAILED DESCRIPTION OF THE PREFERRED EMBODIMENTS

The present invention relates to a novel class of halogenated tetraenyl prostaglandin compounds rerresented by the following general formula

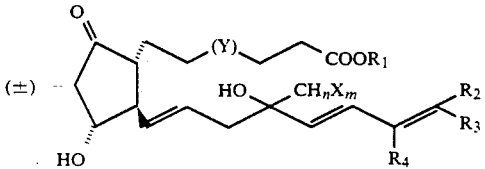

or a pharmaceutically acceptable salt thereof, wherein
Y is —CH=CH— or —CH$_2$—CH$_2$—;
$R_1$ is H or a lower alkyl of 1 to 6 carbons;

n is an integer from 0 to 3;

m is an integer from 0 to 3 and n+m=3;

X is Cl or F provided that when X is Cl, n is 2 and m is 1;

$R_2$ and $R_3$ are independently H, lower alkyl from 1 to 6 carbons, Cl, —$CH_2Cl$, —$CH_2F$, —$CHCl_2$, $CHF_2$, —$CCl_3$, —$CF_3$ or taken together form a cycloalkyl of 3 to 6 carbons;

$R_4$ is H, lower alkyl from 1 to 6 carbons, Cl, F or taken together with $R_3$ form a cycloalkenyl of 4 to 6 carbons; and provided that at least one of —$CH_nX_m$, $R_2$, $R_3$ and $R_4$ includes a chlorine or fluorine atom.

More specifically, the invention herein is directed to a halogenated tetraenyl compound of the formula

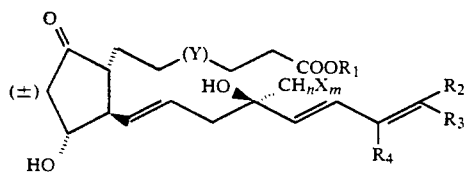

or a pharmaceutically acceptable salt thereof, wherein

Y is —CH=CH— or —$CH_2$—$CH_2$—;

$R_1$ is H or a lower alkyl of 1 to 6 carbons;

n is an integer from 0 to 3;

m is an integer from 0 to 3 and n+m=3;

X is Cl or F provided that n is 2 and m is 1 when X is Cl;

$R_2$ and $R_3$ are H, lower alkyl from 1 to 6 carbons, —$CF_3$, Cl or taken together form a cycloalkyl of 3 to 6 carbons;

$R_4$ is H, lower alkyl from 1 to 6 carbons, F or taken together with $R_3$ form a cycloalkenyl of 4 to 6 carbons; and provided that at least one of —$CH_nX_m$, $R_2$, $R_3$ and $R_4$ includes a chlorine or a fluorine atom.

The invention further relates to pharmaceutical compositions including a compound of formula I or II above and a pharmaceutically acceptable crrier. Such compounds and compositions have shown cytoprotective activity and gastric antisecretory activity with low diarrhea side effects. As such the compounds and the compositions can be useful in the treatment of disorders arising as a result of gastric secretion or which can be treated by the cytoprotective activity offered by the compounds and compositions, such as gastrointestinal ulcers and lesions which can be induced by non-steroidal anti-inflammatory drugs, alcohol and the like.

A preferred embodiment of the compounds herein is a compound of the above formula wherein Y is —CH=CH— and wherein $R_3$ and $R_4$ are taken together to form a cyclopentene ring. Within such preferred embodiment, more preferred compounds include compounds wherein X is F and wherein m is 1 and n is 2; m is 2 and n is 1; or m is 3 and n is 0; or compounds wherein m is 0, n is 3 and $R_3$ is —$CF_3$.

As used herein the term "alkyl" refers to straight or branched chain alkyls such as methyl, ethyl, propyl, isopropyl, butyl, secondary butyl, tertiary butyl, pentyl, or hexyl with the indicated limitation of the number of carbon atoms.

The compounds herein have chiral centers and the invention herein is intended to include the compounds represented by the structures some of which depict racemic mixtures while some of which represent specific isomers. The invention includes the specific isomers and the indicated racemic mixtures. In this regard, in the structures a bond drawn as a straight line is used to indicate no specific spatial/geometric relationship. A bond drawn as a solid triangular shape represents a bond extending upwardly from the plane of the paper and a bond drawn as a dashed triangular shape (not solid) represents a bond extending downwardly from the plane of the paper.

Compounds of this invention are prepared by the following reaction schemes. As can be appreciated by one having skill in the art from a review of the formulas above, more than one reaction scheme can be employed to synthesize the compounds herein. With regard to the following reaction Schemes I-VIII, the following symbols have the following meanings. The symbol Z represents a protecting group and is usually associated with an oxygen atom of a hydroxyl moiety of a compound. Exemplary protecting groups include triethylsilyl and trimethylsilyl.

Y is used as defined above. The symbol X has the meaning defined above.

The symbol Φ is used in these schemes to refer to a phenyl group. The term Bu is used in the schemes to refer to a butyl group. The terms Me and Et are used in the schemes to refer to a methyl or an ethyl group respectively. The other letter symbols appearing in the schemes refer to the respective chemical atoms for which they are generally accepted as standard symbols.

The following reaction Scheme I shows a general reaction scheme for attaching the omega side chain to form the compounds herein. In the reaction scheme a cyclopentenone 1 (with a side chain substituent representing the alpha side chain) is reacted with a particular cuprate 2 to provide the halogenated tetraenyl prostaglandin derivative 3. Simplistically, the cyclopentenone has a substituent group representing the alpha side chain to the prostaglandin analog and the cyclopentenone is reacted with the appropriate cuprate having the desired group representing the omega side chain for the prostaglandin analog 3 to be synthesized.

The preparation of the compounds in Scheme I of the formula 1, the cyclopentene-alkanoic and alkenoic acids and esters, are known. Some syntheses of which are taught in the following U.S. Pat. Nos.: 3,969,391; 3,965,143; 4,060,691; 4,452,994; 4,777,275; 4,075,124; 4,271,314; 4,322,543; 4,477,388; 4,683,328; and 4,952,710. The entire disclosures of each being hereby incorporated by this reference.

Reaction Schemes II and III show varying syntheses for the production of the cuprate compound represented by formula 2 of general reaction Scheme I. The Schemes IV-VIII show various syntheses for the preparation of an equivalent compound to the acetylenically unsaturated compound 4 of Scheme II. In Schemes II through VIII the respective subsequent process steps not shown therein are performed in the same manner as in Scheme I from either compound 2 or as shown in Schemes II or III from compound 4 to produce the prostaglandin derivative having the general formula 3 of Scheme I.

5
SCHEME I
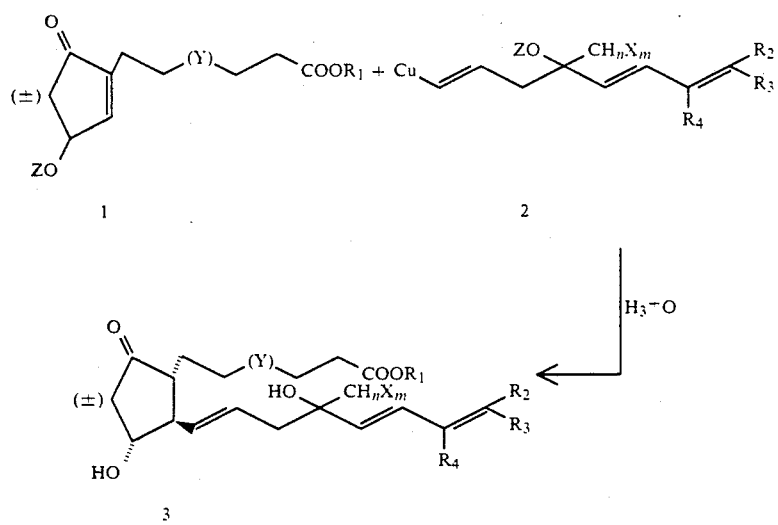
SCHEME II
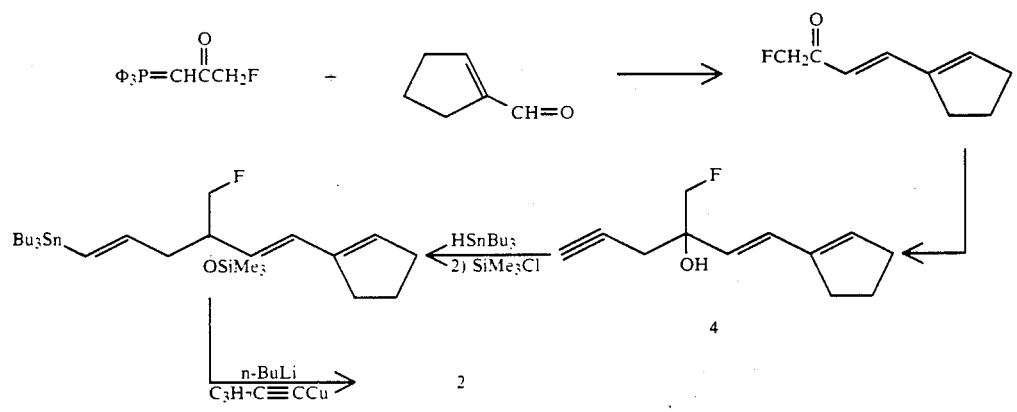
SCHEME III
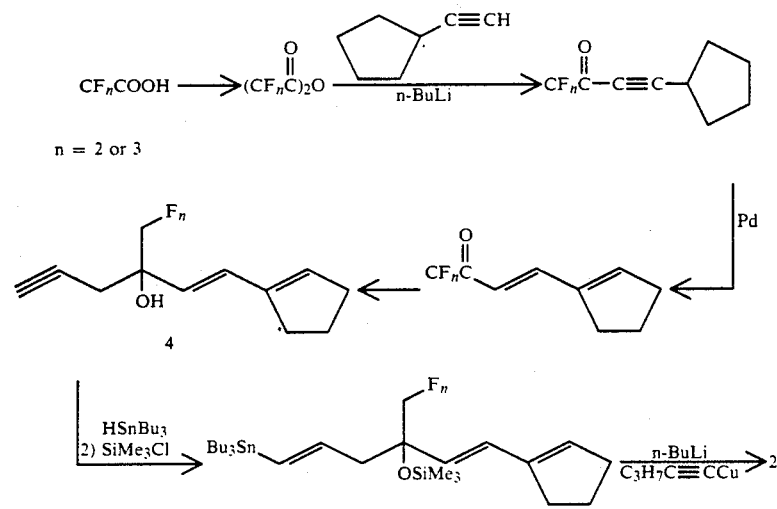

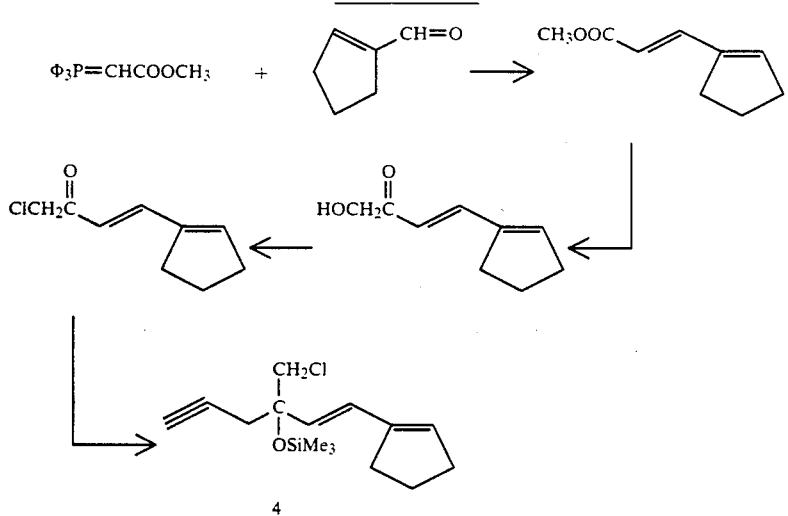
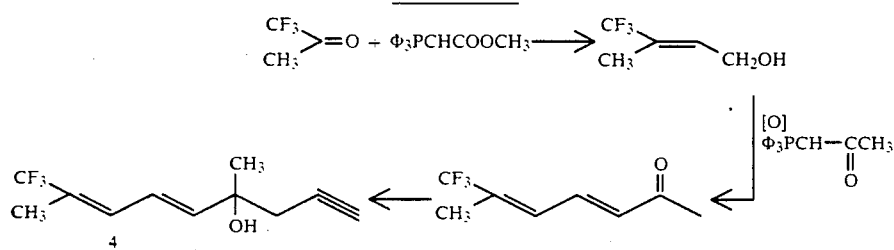
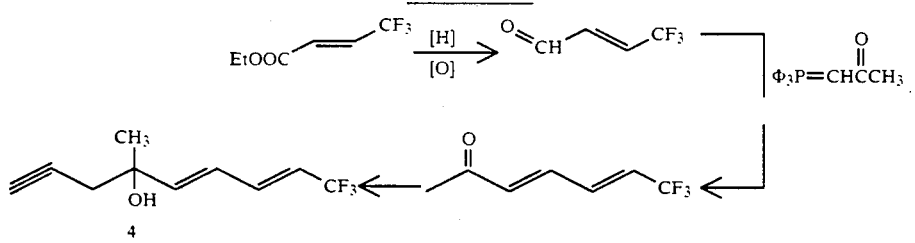
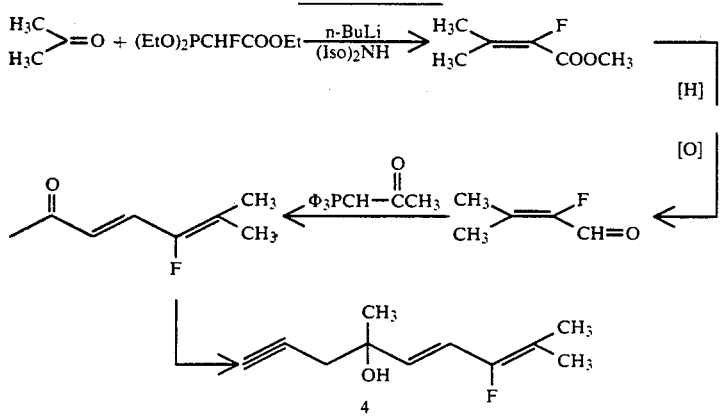

SCHEME VIII

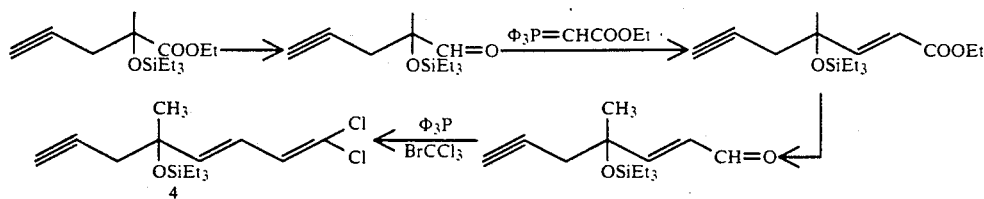

Regardless of the route of administration selected, the novel compounds of the invention herein are formulated into pharmaceutically acceptable dosage forms by conventional methods known to the pharmaceutical art.

The compounds can be administered in such oral unit dosage forms as tablets, capsules, pills, powders, or granules. They can also be administered intraperitoneally, subcutaneously, or intramuscularly, using forms known in the pharmaceutical art. In general, the preferred form of administration is oral. An effective but non-toxic quantity of the compound is employed in the treatment. The dosage regimen for cytoprotection by the compounds of this invention is selected in accordance with a variety of factors including the type, age, weight, sex, and medical condition of the patient, the organ to be protected, the route of administration and the particular compound employed. An ordinarily skilled physician will determine and prescribe the effective amount of the cytoprotective agent required to prevent or arrest the progress of the condition. In so proceeding, the physician could employ relatively low dosages initially, subsequently increasing the dose until a maximum response is obtained. Dosages of the compounds of the invention are ordinarily in the range of 0.05 to 10,000 μg/kg.

The cytoprotective utility of compounds of this invention is illustrated by a standard test which shows their ability to reduce ethanol-induced gastric lesions. In the assay, 0.005-0.5 mg/kg is orally administered to adult 180-220 gram male Charles River rats which have been deprived of food for 24 hours. Thirty minutes later, 1.0 ml of absolute ethanol is administered intragastrically. The rats are sacrificed 60 minutes after alcohol administration and the gastric mucosa are visually examined for the presence of lesions. The number and severity of lesions are scored. A compound is judged active at the concentration evaluated if it provides a statistically significant reduction in the number and/or severity of lesions compared to the control group.

The standard test used to detect gastric antisecretory activity is described as follows.

Adult female beagles, 6-11 kg body weight, were surgically prepared with innervated (Pavlov) gastric pouches that were drained by Thomas-type gastric cannulae. Following surgical recovery, each dog was trained to stand quietly in a dog restraining sling and was conscious for all studies. Experiments began at least 3 weeks after surgery, and no dog was used more than once per week.

Dogs were food-deprived with access to water for 24 hours prior to experiments. Following a 30 minute basal collection period, the prostaglandins or vehicle were administered into the gastric pouch in a 2-3 ml volume. Thirty minutes later the gastric pouch was emptied and gastric secretion was stimulated by feeding 10-12 oz of dog food (Fromm All Beef, Federal Foods Inc., Thiensville, Wis.). Gastric juice samples were collected from the pouch by gravity drainage over a 4 hour period at 30 minute intervals. The volume of secretion was measured (ml/30 min), and the acidity (mequiv/L) was determined by electrometric titration to pH 7.0 with 0.1 N NaOH. These two parameters were multiplied to obtain the total acid output (mequiv/30 minutes) for each collection period.

Percent reduction of total acid output from control was calculated over each 4 hour experiment for doses of prostaglandin. $ED_{50}$ values and 95% confidence limits were determined from inhibition of secretion curves.

Diarrhea is an undesirable side effect commonly associated with antisecretory and cytoprotective prostaglandins. Diarrheagenic activity is demonstrated by the following standardized test. Groups of 6 adult male Charles River rats weight rang®180 to 200 g, are fasted for 24 hours prior to administering the test substance. The prostaglandin to be tested is administered intragastrically in iso-osmotic phosphate buffer at a volume of 10 ml/kg at doses ranging from 100 to 3000 μg/kg. Control animals receive only the vehicle. The rats are placed in individual wire mesh cages and the trays lined with brown paper. Diarrhea is assessed at hourly intervals on all or none basis for up to 8 hours after administration of the prostaglandin. Diarrhea is defined as any loose or watery stool. $ED_{50}$ values are assessed for each hourly diarrheagenic response.

The following examples illustrate the present invention and are not intended to limit the invention in spirit or scope. Temperatures, where given, are in degrees centigrade unless otherwise indicated.

EXAMPLE 1

(±)-methyl 7-[2β-[6-(1-cyclopenten-1-yl)-4R-(fluoromethyl)-4-hydroxy-1E,5E-hexadienyl]-3α-hydroxy-5-oxo-lo-cyclopentyl]-4Z-heptenoate

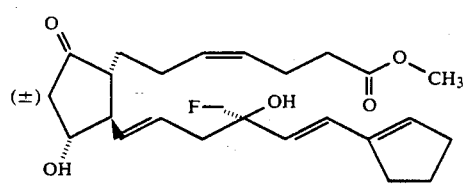

The above compound is prepared in accordance with the procedure generally shown in Scheme II and in Scheme I. A 100 ml single neck round bottom flask fitted with a stirring bar and condenser was charged with 1.63 g (17 mmoles) of cyclopentenecarboxaldehyde (commercially available). The flask was also charged with 6.79 g (20.2 mmoles) of 1-(fluoroacetyl)-methylenetriphenylphosphorane which was prepared by a known technique (J. Leroy, C. Wakselman, *Synth.* 496 (1982). To the reaction flask was added 43 ml of toluene. The toluene and the reaction mixture was heated to reflux for a reaction time of 23 hours. The toluene was stripped off on a rotary evaporator and the residue slurried in 50 ml of a 10% ethyl acetate/hexane solution. The triphenylphosphorane crystallized and was filtered off and collected. The filtrate was washed a second time with 10% ethyl acetate/hexane mixture. The ethyl acetate/hexane was stripped on a rotary evaporator. The residue was dissolved in 30 ml benzene which was stripped on a rotary evaporator. The benzene wash was repeated twice. The resultant fluoroketone was purified on a chromatography column of silica gel with 2% ethyl acetate-toluene. 1.42 g of a yellow oil of the fluoroketone of the following formula was obtained.

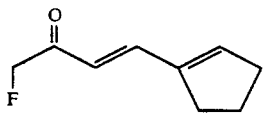

The fluoroketone was reacted with propargyl bromide in a Grignard reaction in the following manner.

In a 3 neck 50 ml round bottom flask fitted with an argon inlet tube, stirring bar, stopper, digital thermometer was introduced 196 mg (8.08 mmoles) of magnesium powder, 8 ml dry THF, and 10 to 20 milligrams of mercuric chloride as a catalyst. To the mixture was added dropwise 961 mg (8.08 mmoles, or 610 $\mu$l ) of propargyl bromide. The temperature of the solution was maintained at 35° C. to 45° C. and was stirred vigorously. After the Grignard formation was complete the mixture was cooled to −78° C. To the propargyl Grignard reagent was added 623 mg (4.04 mmoles) of the fluorodienone prepared above in 6 ml dry THF by dropwise addition at −78° C. The temperature maintained less than −70° C. After the reaction was complete (TLC) the reaction mixture was quenched by adding dropwise 300 mg (5mmol) of acetic acid dissolved in 2 ml of THF at −78° C. The reaction mixture was diluted with about 15 ml of diethyl ether maintaining the temperature at −78° C. To the solution was added 5 ml of saturated ammonium chloride solution and the reaction mixture was allowed to warm to −20° C. The reaction mixture was poured into a stirred mixture of 50 ml saturated ammonium chloride solution and 200 ml of diethyl ether. The layers formed were separated and the diethyl ether layer was washed with saturated ammonium chloride solution, dilute sodium carbonate solution, water and brine. The combined aqueous wash was back extracted with 40 ml of diethyl ether. The diethyl ether fractions were combined and dried over magnesium sulfate. The fluoromethyl acetylenic alcohol formed was purified via chromatography on a silica gel column using a 15% ethyl acetate/hexane solution 835 mg of the fluoromethyl acetylenic alcohol was recovered following chromatography.

The fluoromethyl acetylenic alcohol was hydrostannated as shown in Scheme II. To a 10 ml round bottom flask fitted with an argon inlet tube and stirring bar was charged 750 mg of the fluoromethyl acetylenic alcohol formed above. To the flask was added 1.184 g (4.07 mmoles) of tri-n-butyl tin hydride. A catalytic amount of about 5 mg of azobisisobutyronitrile (AIBN) was added and the reaction flask was irradiated with ultraviolet light (sunlamp). At 2 hours 4 drops of Bu₃SnH was added. At 3 hours 6 drops were added, at 5 hours 4 drops were added and 6 hours an additional 4 drops were added. The hydrostannated product was purified on silica gel pretreated with 50% ethyl acetate/hexane/100% ethyl acetate/50%ethyl acetate-hexane/10% ethyl acetate/hexane and eluting with 10% ethyl acetate/hexane. Purification provided 1.40 g of a clear colorless oil of the hydrostannated product.

A trimethylsilyl protecting group was added to the tributylstannane product in the following manner. Into a reaction flask was added 1.39 g (2.86 mmoles) of vinylstannane, 8 ml dimethylformamide (DMF) and 402 mg (3.7 mmoles) of trimethylchlorosilane (Me₃SiCl). To the flask was also added 449 mg (6.6 mmoles) of imidazole. After 1 hour at room temperature the reaction mixture was poured into a mixture of 100 ml of diethyl ethyl/100 ml of water and the resultant layers separated. The aqueous layer was back extracted 3 times with 25 ml portions of a 1 to 1 mixture of diethyl ether and hexane The combined organic layers were washed 3 times with water and once with brine. The ether layer was dried over magnesium sulfate. The magnesium sulfate was filtered off and the ether stripped to yield 1.51 g of a clear oil which was the protected product.

The cuprate was formed in the following manner. To a 25 ml round bottom flask fitted with an argon inlet tube, stirring bar, serum cap, and digital thermometer probe was added 750 mg (1.35 mmoles) of the protected vinylstannane prepared above in 4 ml THF. The solution was cooled to −78° C. and to it was added 844 $\mu$l of 1.6 M n-butyllithium with stirring for 15 minutes at −78° C. An additional 42 $\mu$l was added with stirring over 10 minutes. In a second single neck round bottom flask with an argon inlet tube and a stirring bar was added 176 mg (1.35 mmoles) of copper pentyne and 4 ml of diethyl ether and 441 mg or 491 $\mu$l (2.7 mmoles) of hexamethylphosphorous triamide. The reaction mixture was stirred for ½ hour at room temperature and the resultant solution added to the flask containing the vinyl lithium solution at −78° C. The reaction mixture was stirred for 20 minutes at −78° C. and allowed to warm to −55° C. To the flask was added 238 mg of the racemic cyclopentenone (Compound 1 of Scheme 1) in 2 ml of dry THF via syringe at −78° C. The reaction mixture was stirred for 20 minutes after the addition. The cold reaction mixture was poured into 80 ml of a 7 to 1 saturated ammonium chloride solution/concentrated ammonium and 150 ml of diethyl ether. The mixture was stirred vigorously for 20 minutes and the aqueous layer was drawn off. The aqueous layer was extracted twice with 50 ml portions of diethyl ether. The organic extracts were combined and washed with saturated ammonium chloride solution, dilute sodium bicarbonate solution, water, and brine. The ether layer was dried over magnesium sulfate.

The resultant product was purified on a silica gel column using an eluant of 9% ethyl acetate/hexane. The product recovered was the protected prostaglandin analog of the above formula. The product was deprotected by dissolving 615 mg of the purified oil in 100 ml of a 9 to 1 acetone-water mixture and adding 100 mg of pyridinium p-toluenesulfonate (PPTS). After 5 hours the acetone was stripped off on a rotary evaporator and to the reaction mixture was added 200 ml diethyl ether and 30 ml of water. The layers were separated and the ether layer was washed once with sodium bicarbonate solution. The aqueous layer was washed twice with 30 ml portions of diethyl ether. The ether layers were combined and washed twice with water and once with brine. The ether layer was dried over magnesium sulfate. The magnesium sulfate was filtered off and the ether was stripped off yielding 605 mg of the product as an oil.

This product consisting of 2 diastereoisomers was chromatographed on silica gel using 65% ethyl acetate/hexane as eluant to give the individual diastereomers with the product having the stereochemistry indicated in the above formula eluting second.

¹H NMR(CDCl₃): δ2.23(dd,1H,10αH); 2.73(dd,1H,10βH); 3.68(s,3H,OCH₃); 4.04(q,1H,11H); 4.30(d,2H,CH₂F); 5.33(m,2H,4,5H's); 5.48(d,1H,17H); 6.58(d,1H,18H).

EXAMPLE 2 methyl 7-[2β-[6-(1-cyclopenten-1-yl)-4R-(fluoromethyl)-4-hydroxy-1E,5E-hexadienyl]-3α-hydroxy-5-oxo-1R,1α-cyclopentyl]-4Z-heptenoate

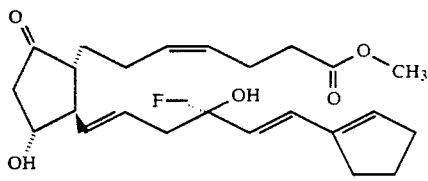

The product prepared in this example is a specific stereoisomer prepared from resolved (11R)-cyclopentenone according to the procedures of Example 1. The isomer was separated from its diastereoisomer by chromatography on silica gel using 65% ethyl acetate/hexane as an eluant. The second diastereoisomer recovered from the column was the above product. The product as noted above was assigned the 11(R), 16(R) configuration, based on elution sequence and biological activity.

¹H NMR(CDCl₃): δ2.23(dd,1H,10αH); 2.73(dd,1H,10βH); 3.68(s,3H,OCH₃); 4.04(q,1H,11H); 4.30(d,2H,CH₂F); 5.33(m,2H,4,5H's); 5.48(d,1H,17H); 6.58(d,1H,18H).

EXAMPLE 3

(±)-methyl 7-[2β-[6-(1-cyclopenten-1-yl)-4R-(difluoromethyl)-4-hydroxy-1E,5E-hexadienyl]-3α-hydroxy-5-oxo-1α-cyclopentyl]-4Z-heptenoate

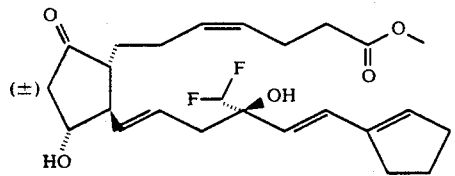

This example is directed to the difluoromethyl analog of the compound of Example 1. The compound is prepared in the manner disclosed in Schemes III and I. A mixture of 50 g of difluoroacetic acid (521 mmoles) and 37 g phosphorous pentoxide (P₂O₅) was refluxed for 3 hours. The reaction mixture was cooled and an additional 9 g of P₂O₅ (total 324 mmoles) was added. The reaction mixture was distilled at atmospheric pressure and a product recovered at a boiling point of 123°–125° C. The difluoroacetic anhydride was collected as a clear liquid, 35.5 g. In a flame dried apparatus was added dropwise 47 ml of 1.6M n-butyl lithium to a solution of 7.5 g cyclopentyl acetylene (commercially available) in 100 ml THF under argon cooled to −30° C. After the addition was completed the reaction mixture was stirred for ½ hour while allowing the mixture to warm to 0° C. In a second flame dried apparatus under argon was placed a solution of 35.5 g difluoroacetic anhydride in 200 ml THF and chilled to −65° C. The acetylide solution was added dropwise to the anhydride solution over 2 hours maintaining the temperature below −60° C. The reaction mixture was stirred for another 1 hour after the addition was completed, and the reaction mixture was poured into a solution of 45 g sodium bicarbonate in 500 ml of water. The mixture was stirred for 30 minutes and extracted 3 times with ether and the ether extracts combined, washed once with sodium chloride solution and dried over magnesium sulfate. The ether was evaporated and the residue flash chromatographed using 5% ethyl acetate-hexane to afford 8.3 g of the 4-cyclopentyl but-3-yne-1-difluoromethyl-2-one product. The resultant ketone was isomerized by mixing 1.5 g (7.9 mmoles) of the ketone with 89 mg (0.4 mmoles) palladium(II) acetate, 734 mg (2.8 mmoles) of triphenylphosphine in 15 ml of toluene. The reaction mixture was refluxed for ½ hour. The reaction mixture was cooled and applied directly onto a silica gel column and eluted with 100% hexane until the triphenylphosphine was removed. The eluant was increased to 2% ethyl acetate in hexane. The product 4-(1-cyclopentene)-1-trifluoromethylbut-3-ene-2-one was recovered in an amount of 1 g.

The difluorodiene ketone was then reacted through a Grignard reaction in the manner set forth in Example 1 subsequently followed by the hydrostannation reaction, followed by the cuprate reaction to yield the above identified final product.

The analysis of the final product was

¹H NMR (CDCl₃): δ 3.67S(C-1 OCH₃); 5.59 t, J=57Hz(CHF₂); 5.51 d, J=15.5Hz(C-17H); 6.64 d, J=15.5Hz(C-18H)

¹³C NMR: δ 51.6 (OCH₃); 173.9(C-1); 214.7(C-9) 71.9(C-11); 117.4(CHF₂, $J_{cf}$=250 Hz)

EXAMPLE 4

(±)-methyl 7-[2β-[6-(1-cyclopenten-1yl)-4R-hydroxy-4-(trifluoromethyl)-1E,5E-hexadienyl]-3α-hydroxy-5-oxo-1α-cyclopentyl]-4Z-heptenoate

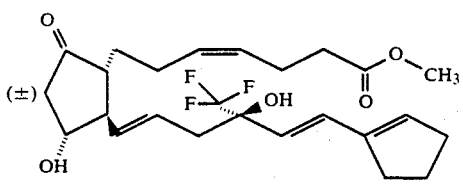

The procedure of Example 3 was repeated in every essential detail with the exception that the initial acetic acid product was trifuloroacetic acid. The above 16-trifluoromethyl product resulted.

¹H NMR (CDCl₃): δ 3.67 s(C-1 OCH₃); 5.51 d, J=15.8Hz(C-17H); 6.68 d J=15.18Hz(C-18H)

¹³C NMR: δ 51.7(OCH₃); 214.4(C-9); 72.0(C-11) 125.3(CF₃ $J_{CF}$=286 Hz); 75.4 (C-16 $J_{CCF}$=28 Hz); 135.2(C-17); 124.6(C-18)

EXAMPLE 5

(±)-methyl 7-[2β-[4R-(chloromethyl)-6-(1-cyclopenten-1-yl)-4-hydroxy-1E, 5E-hexadienyl]-3α-hydroxy-5-oxo-1α-cyclopentyl]-4Z-heptenoate

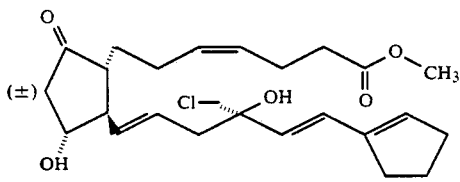

Methyl 3-(1-cyclopentenyl)-trans-2-propenoate. 1-cyclopentene-1-carboxaldehyde (9.60 g, 100 mmoles) was mixed with methyl (triphenylphosphoraylidene) acetate (40.1 g, 120 mmoles) in 80 ml of benzene and was brought to reflux under nitrogen for 5 hours. After cooling, the solids were filtered off, washed with ether and discarded. The solvent mixture was concentrated in vacuo, triturated with several volumes of pentane, filtered and stripped. Flash chromatography on silica gel afforded 14.8 g of the desired ester as a pure, white solid.

3-(1-cyclopentenyl)-trans-2-propenoic acid. The above methyl ester (6.08 g, 40 mmoles), 16 ml of methanol and 40 ml THF were mixed and cooled to 0° C. under nitrogen. To the solution was added 60 ml of 1.0 N lithium hydroxide and the mixture was stirred at ambient temperature overnight. The solvent was concentrated in vacuo, diluted with an equal volume of water and washed with 1 volume of ether. The aqueous mixture was acidified using 2N HCl, saturated with solid NaCl, extracted with 3 volumes of ether and dried over magnesium sulfate. After removal of the solvent via rotary evaporation, 4.22 g of the desired acid was obtained as a white solid.

t-Butyldimethylsilyl 3-(1-cyclopentenyl)-trans-2-propenoate. The propenoic acid (4.0 g, 29 mmoles) and imidazole (2.72 g, 40 mmoles) were dissolved in 25 ml dry DMF under nitrogen followed by the addition of t-butyldimethylchlorosilane (4.82 g, 32 mmoles) and stirred for 3 hours at ambient temperature. The mixture was poured into cold, dilute sodium bicarbonate solution and extracted with 2 portions of 1:1 etherhexane. The combined organic extracts were washed with successive portions of dilute sodium bicarbonate solution, brine and dried over sodium sulfate. The solvent was removed via rotary evaporation and the crude silyl ester was used without further purification.

4-(1-Cyclopentenyl)-trans-3-butene-2-one-1-ol. The above silyl ester (6.97 g, 27.4 mmoles) was mixed with 120 ml methylene chloride and cooled to 0° C. under nitrogen. Oxalyl chloride (4.18 g, 33 mmoles) was added followed by 0.5 ml dry DMF. A vigorous reaction with rapid bubbling ensued. After the bubbling ceased, the mixture was warmed to room temperature. The solvent was removed via rotary evaporation. The crude mixture was combined with 75 ml chlorobenzene, tris(trimethylsiloxy)ethylene (16.1 g, 55 mmoles) and brought to reflux under argon for 5 hours. After cooling, the solvent was removed in vacuo via rotary evaporation after which the dark mixture was combined with 50 ml dioxane and 50 ml 1N HCl and stirred at room temperature under argon overnight. Solid NaCl was added and the mixture poured into a large volume of ethyl acetate. The organic layer was washed with successive portions of dilute sodium bicarbonate solution, brine and dried over magnesium sulfate. Solvent removal followed by chromatography on silica gel gave 0.51 g of the above named alcohol as a pale yellow solid.

1-Chloro-4-(1-cyclopentenyl)-trans-3-butene-2-one. Carbon tetrachloride (1.172 g, 11.2 mmoles) was combined with triphenylphosphine (2.72 g, 10.4 mmoles) in 15 ml of methylene chloride under argon. To the mixture was added the above recovered butenone alcohol (0.79 g, 5.2 mmoles) and the mixture was stirred at room temperature for 3 hours. After solvent removal and chromatographic purification on silica gel, 0.61 g of the desired chloromethyl ketone was recovered as a pale yellow solid.

4-Chloromethyl-4-hydroxy-6-(1-cyclopentenyl)-trans-5-hexene-1-yne. To a freshly activated suspension of #40 magnesium powder (0.11 g, 4.5 mmoles) in dry THF under argon, neat propargyl bromide was added slowly, maintaining the reaction temperature below 45° C. for 1 hour and then cooled to below −70° C. The chloromethyl ketone recovered above (0.31 g, 1.8 mmoles) was added in 2 portions and the mixture stirred for 45 minutes then rapidly quenched with saturated ammonium chloride solution. The mixture was extracted with 2 portions of ether, followed by washing with 1 portion of brine and dried over sodium sulfate. After solvent removal and chromatographic purification on silica gel, 0.31 g of the desired chloromethyl hexynol was obtained as a white solid.

4-Chloromethyl-4-trimethylsilyloxy-6-(1-cyclopentenyl)-trans-5-hexene-1-yne. The above recovered chloromethyl hexynol (0.61 g, 2.9 mmoles) and imidazole (0.34 g, 5.0 mmoles) were dissolved in 6 ml dry DMF under argon and treated with chlorotrimethylsilane (0.43 g, 4.0 mmoles) for 3 hours at room temperature. The mixture was poured into cold, dilute sodium bicarbonate solution and extracted by 2 portions of 1:1 ether-hexane. The combined organic extracts were washed with successive portions of dilute sodium bicarbonate solution, brine and dried with sodium sulfate. After solvent removal and chromatographic purification on silica gel, 0.71 g of the TMS ether were obtained as a colorless oil.

Disilyl prostaglandin. To a solution of the TMS ether recovered above (0.36 g, 1.25 mmoles) in 6 ml dry THF under argon at room temperature, zirconocene chlorohydride (0.38 g, 1.4 mmoles) was added in 2 successive and equal portions. When all of the solids were dissolved, the mixture was cooled to below −70° C. Solid copper(I) cyanide was added followed by a slow addition of methyl lithium (3.7 ml, 4.1 mmoles) in cumene-THF. After the solution became clear (approximately 30 minutes), a THF solution of cis delta 4,5-triethylsilyl cyclopentenone methyl ester (0.22 g, 0.62 mmoles) was added. After 30 minutes, the reaction was rapidly quenched by pouring into a stirred mixture of 9:1 saturated ammonium chloride-concentrated ammonium hydroxide solution. The resultant mixture was extracted with 2 portions of 1:1 ether-hexane. The combined organic extracts were filtered and washed with successive portions of saturated ammonium chloride solution, brine and dried with sodium sulfate. After solvent removal and chromatographic purification on silica gel, 0.27 g of disilyl prostaglandin was obtained as a colorless oil.

16-Chloromethyl prostaglandin. The disilyl prostaglandin recovered above (0.27 g) was mixed with 20 ml acetone and 2 ml of water under argon and treated with pyridinium p-toluenesulfonate (25 mg) at room temperature overnight. The reaction was quenched with solid sodium bicarbonate, filtered and concentrated by rotary evaporation. The mixture was taken up in ethyl acetate, washed with saturated sodium chloride solution and dried with sodium sulfate. Solvent removal followed by chromatographic purification on silica gel gave 37 mg of the desired 16-chloromethyl prostaglandin. $^1$H NMR: δ 3.67, s 3H; 5.33,m,2 H; 4.04,q,1H; 5.48,dd,1H; 5.67,dt,1H; 3.58,s,2H; 5.51,dd,1H; 6.68,dd,1H; 5.78,broad s,1H.

EXAMPLE 6

(±)-methyl 11α,16R-dihydroxy-16-methyl-9-oxo-20-(trifluoromethyl) prosta-4Z,13E,17E,19E-tetraen-1-oate

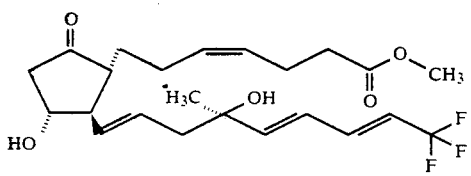

The above identified 20-trifluoromethyl prostaglandin analog was prepared following the procedure shown in reaction Scheme VI and as shown, subsequently, in reaction Schemes II and I. In a 500 ml 3 neck round bottom flask fitted with an argon inlet tube, dropping funnel and low temperature thermometer were added 15.46 g (92 mmoles) of ethyl 4-trifluorobut-2-enoate and 100 ml of dichloromethane. The dropping funnel contained 200 ml of 1 M DIBAL (diisobutyl aluminum hydrided) in dichloromethane (200 mmoles, 2.2 equivalents). The DIBAL solution was added to the ester at 0° C. dropwise over ½ hour. The reaction mixture was allowed to warm to 20° C. following the addition. The reaction mixture was cooled in an ice bath and a saturated ammonium chloride solution (30–50 ml) was added dropwise. To the resultant slurry was added 2 M HCl(300 ml) with agitation. The clear solution was transferred to a separatory funnel and the dichloromethane removed. The aqueous layer was extracted with 75 ml dichloromethane which was combined with the previously collected dichloromethane. The dichloromethane solution was washed with sodium bicarbonate and dried over magnesium sulfate. The dichloromethane was distilled off and the resulting residue distilled with the trifluorobut-2-enol collected at 120°–126° C. yielding 8.51 g of a clear liquid.

1-trifluoro-hept-(3,5)-dien-2-one. In a dry 1 liter 3 neck round bottom flask fitted with a gas inlet tube, magnetic stirrer, 125 ml dropping funnel and low temperature thermocouple probe were added 500 ml of dichloromethane and 5.88 ml oxalyl chloride. The mixture was cooled in a dry ice/acetone bath to −76° C. To the flask was added 9.57 ml of dimethylsulfoxide (DMSO) in 50 ml of dichloromethane dropwise with stirring. The temperature was maintained at less than −70° C. The mixture was stirred for 15 minutes and 7.09 g of the above allyl alcohol added in 50 ml dichloromethane dropwise slowly. To the mixture was added 39.2 ml of triethylamine (neat) dropwise. The temperature was allowed to warm to −15° C. To the solution was added 21.5 g (67.4 mmoles) of triphenylphosphoranylidene-2-propanone and the reaction mixture was allowed to warm to room temperature with stirring. The reaction mixture was poured into equal volumes of 0.5N HCl and shaken vigorously and the layers allowed to separate. The acidic layer was extracted with 150 ml of dichloromethane. The dichloromethane was washed once with sodium bicarbonate and once with brine then dried over anhydrous magnesium sulfate. The dichloromethane was distilled leaving a residue which was triturated with 400 ml of pentane and filtered. The filtrate was collected and stripped of the pentane by distillation to yield 9.98 g of a red oil. A second distillation provided 7.0 g of a clear oil, b.p. 74°–81° C., at 16 mm Hg.

1-trifluoro-6-hydroxy-6-methyl-octa-(2,4)-diene-8-yne. To a flame dried 100 ml 3 neck round bottom flask equipped with an argon inlet tube, magnetic stirring bar, condenser and 25 ml dropping funnel were added 729 mg (30 mmoles) of magnesium turnings. 30 ml of dry THF were added to the flask. From the dropping funnel was added dropwise a mixture of 4.10 g (25 mmoles) of the ketone formed above, 3.27 g (27.5 mmoles) of propargyl bromide and 8 ml of dry THF. The reaction was initiated by adding about 5 ml of the total 15 ml of ketone, bromide and THF. The reaction mixture was stirred at room temperature and a catalytic amount of mercuric chloride (a few mg) was added. THF was added to aid in initiating the reaction. The solution changed from a light yellow to a dark red brown and began to reflux. As reflux began the remainder of the ketone, bromide and THF was added dropwise with stirring and maintaining the temperature at room temperature until addition was complete. The reaction mixture was poured into 400 ml of a 1:1 1N HCl/ether mixture and shaken. The resultant aqueous layer was extracted with 100 ml of ether. The ether layers were combined and washed twice with 100 ml of water, once with 15 ml of saturated sodium bicarbonate solution and once with 50 ml of brine. The ether layer was dried over anhydrous magnesium sulfate, filtered, and evaporated yielding 4.94 g of a red oil. The oil was purified on silica gel using 20% ethyl acetate/hexane as eluant.

A triethylsilyl protecting group was added to the hydroxyl moiety by taking 503 mg (2.46 mmoles) of the acetylenic diene alcohol and dissolving in 9 ml of dry DMF in a 250 ml round bottom flask fitted with a magnetic stirring bar and gas inlet tube. To the mixture was added 375 mg (5.5 mmoles) of imidazole. Also added to the mixture was 553 mg (3.67 mmoles) of triethylsilyl chloride. The reaction mixture was poured into a mixture of 50 ml of water and 50 ml of a 1:1 mixture of ether/hexane. The layers were allowed to separate and the aqueous layer extracted twice with 25 ml portions of a 1 to 1 mixture of ether-hexane. The combined ether-hexane layers were washed once with 50 ml of water and once with brine and dried over magnesium sulfate. The layers were filtered and stripped of solvent yielding 617 mg of a yellow oil. The oil was purified on silica gel using 0.75% ethyl acetate-hexane as eluant to yield 455 mg of a colorless oil.

Hydrozirconation/iodination sequence. 448 mg (1.41 mmol) of the triethylsilyl protected acetylenic diene was dissolved in 5 ml of benzene. To the solution was added 478 mg (1.85 mmol) of zirconocene chloride hydride. The reaction mixture was stirred over argon for approximately 5 hours. To the mixture was added 3 ml dry THF and the mixture cooled in an ice bath. To the mixture was added dropwise 317 mg (1.41 mmol) of N-iodosuccinimide in 4 ml of dry THF. Following the addition the mixture was allowed to warm to room temperature and poured into a mixture of 50 ml ether and 25 ml of water. Upon separation of the layers, the aqueous layer was extracted once with 25 ml of ether. The combined ether layers were washed twice with 25 ml water, dried over magnesium sulfate, filtered and stripped to yield 610 mg of a crude red oil. Silica gel purification With an eluant of 0.5% ethyl acetate/hexane yielded 272 mg of the trans vinyl iodide of the formula

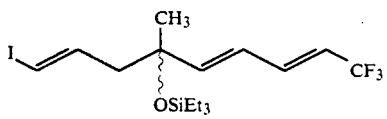

The 272 mg (0.61 mmol) of the trans vinyl iodide was dissolved in 2 ml of dry THF in a 25 ml single neck round bottom flask topped with an argon inlet tube and drying tube. The mixture was cooled to −75° C. To the mixture was added 1.6 mol (0.38 ml) of n-butyllithium and stirred for 15 minutes. In a 10 ml single neck round bottom flask fitted with a stirring bar and topped with a nitrogen inlet tube was added 79.7 mg of copper(I) pentyne (0.61 mmol). To the flask was added 199 mg (1.22 mmol) of HMPT (hexamethylphosphorus triamide) dissolved in 2.0 ml ether and stirred at room temperature for 15 minutes. An additional five drops of HMPT were added to solubilize the copper pentyne. The copper pentyne solution was added via syringe to the cold THF solution of the vinyl lithium at −75° C. The reaction mixture was stirred for fifteen minutes at −70° C. and then treated with 144.5 mg (0.41 mmol) of the cyclopentenone in 1 ml dry ether via syringe at −70° C. The resultant mixture was stirred for ½ hour at −70° C. then poured into a mixture of 50 ml ether/50 ml 1 N HCl and shaken. The ether layer was washed twice with two 50 ml. portions of water and dried over anhydrous sodium sulfate. The ether layer was filtered and stripped of solvent to yield 379 mg of a crude yellow oil. The oil was purified using silica gel chromatography eluting with 10% ethyl acetate/hexane to give 148 mg of a light yellow oil.

The oil was deprotected by dissolving 148 mg (0.22 mmol) of the oil in 3 ml of a 9:1 acetone-water mixture. To the mixture was added 1 to 2 mg pyridinium p-toluenesulfonate. The reaction mixture was allowed to stand at room temperature for 35 hours and then poured into 40 ml of ether and washed once with 20 ml water. The aqueous layer was extracted once with 10 ml of ether and the ether layers combined and washed once with dilute sodium bicarbonate solution, with brine and dried over magnesium sulfate. The resultant product was purified by column chromatography using a solvent of 75% ethyl acetate/hexane and yielded 25 mg of the above-identified product.

$^1$H NMR(CDCl$_3$): δ1.33(s,3H,16-Me); 2.22,(dd,1H,10αH); 2.73(dd,1H,10βH); 3.66(s,3H,OCH$_3$); 4.04(q,1H,11H); 5.32(m,2H,4,5H's); 6.08(d,1H,17H); 6.31(dd,1H,18H); 6.73(dd,1H,19H).

EXAMPLE 7

(±)-methyl 11α,16R-dihydroxy-16,20-dimethyl-9-oxo-20-(trifluoromethyl) prosta-4Z,13E,17E, 19E-tetraen-1-oate

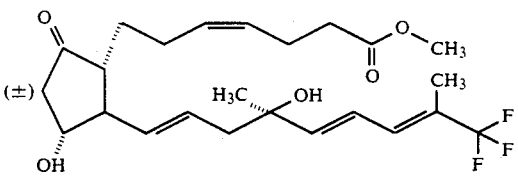

The above-identified 20-methyl, 20-trifluoromethyl prostaglandin was prepared in accordance with Scheme V followed by the procedures in Schemes II and I. Into a flask was placed 10.03 gm (30 mmol) of methyl (triphenylphosphoranylidene) acetate suspended in 50 ml of ether. To the flask was added 2.89 gm (25 mmol) of 1,1,1-trifluoro acetone dropwise at room temperature. The mixture was stirred at room temperature overnight, the solids were filtered and washed with ether. The filtrate and ether wash were combined and diluted with approximately 3 volumes of pentane and stirred at 0° C. for approximately one hour. The mixture was filtered and the excess solvent distilled off at atmospheric pressure. The mixture was transferred to a flask and distilled further to remove all pentane and ether yielding 2.82 gm of the methyl 3-trifluoromethyl but-2-enoate. 11.2 gm (from a larger preparation) (66.7 mmol) of the ester was mixed with approximately 10 ml of dichloromethane and cooled to −5° C. To the mixture was added DIBAH dropwise (146.7 ml, 146.7 mmol) and the mixture stirred at room temperature for 2 hours. The mixture was cooled to 0° C. and a solution of saturated ammonium chloride was slowly added. The solution warmed to 25°. The mixture was transferred to a separatory funnel and the dichloromethane layer removed. The aqueous layer was re-extracted with dichloromethane and the combined organic extracts were dried over magnesium sulfate. The solvent was distilled off at atmospheric pressure yielding 6.8 gm of the 3-trifluoromethyl but-2-en-1-ol. In a flame-dried 250 ml flask under argon, 0.84 ml (9.8 mmol) of oxalyl chloride and 70 ml of methylene chloride were mixed and cooled to less than −60° C. A solution of 1.31 ml (19.4 mmol) of dimethylsulfoxide (DMSO) in dichloromethane (20 ml total volume) was added slowly. The butenyl alcohol (1.12 gm, 80 mmol) was dissolved in dichloromethane (about 50 ml and added slowly to the solution. After 15 minutes, 5.6 ml (40 mmol) of triethylamine was added. The temperature was raised to −15° C. and 3.18 gm (10 mmol) of 1-triphenyl phosphoranylidene-2-propanone was added. The mixture was stirred at room temperature for approximately 1 hour and poured into cold water, shaken and extracted with diethyl ether. The organic layer was washed with dilute sodium chloride solution followed by a saturated sodium chloride solution, then dried over magnesium sulfate. The mixture was concentrated and the concentrate mixed with 10 volumes pentane and placed at −20° C. overnight. The solids were filtered off and washed with pentane. The organic solutions were combined and evaporated to yield 6-trifluoromethyl(3,5)-hepta-diene-2-one (3.66 gm of a pale yellow oil).

The Grignard step was performed by flame drying 40 mesh magnesium (0.90 gm, 37 mmol) under argon adding 100 ml of THF and activating the magnesium with small amounts of iodine and mercuric chloride. Propargyl bromide (3.26 gm, 27.4 mmol) was mixed with THF and added to the activated magnesium until the temperature had risen to 40° C. The above ketone and remaining THF were added to the reaction mixture and the temperature maintained around 45° C. The mixture was stirred at ambient temperature for approximately 90 minutes and poured into concentrated ammonium chloride to quench. Ether was added to the mixture and the organic layer removed and washed with concentrated ammonium chloride, saturated sodium chloride and dried over magnesium sulfate. Evaporation of solvents provided 8.15 gm of a brown oil which, following purification by silica gel chromatography, yielded 3.2 gm of 8-trifluoromethyl-4-hydroxy-4-methyl-5,7-diene-1-nonyne. The nonyne (1.23 gm, 5.65 mmol) was mixed with 2.06 gm of tri-butyltin hydride and a trace of AIBN and irradiated using ultraviolet light (sunlamp) for 8 hours. An additional 0.5 equivalents of the tin hydride was added with continued irradiation for a total of 19 hours. The resulting product had the following structure.

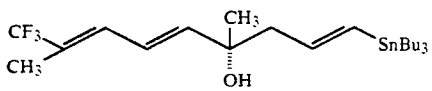

The product was protected with a trimethylsilyl protecting group by treating 0.91 gm of the alcohol (1.78 mmol) with 0.20 gm (1.88 mmol) of trimethylchlorosilane, 170 mg of imidazole (2.5 mmol) and 3 ml of DMF. After about 1 hour, the reaction was worked as usual and 1.01 gm of product obtained. The 1.01 gm (1.7 mmol) of the TMS vinyl tin product was reacted with 1.06 ml (1.7 mmol) of n-butyllithium followed by addition of 0.248 gm of pentynyl copper (1.9 mmol) solubilized with 0.81 gm of HMPT in 12 ml ether and then 352 mg of cyclopentenone. The resulting prostaglandin product (110 mg) was deprotected using acetone/water mixture (6 ml) and PPTS (a trace, approximately 5 mg) yielding 24.6 mg of the title compound.

$^1$H NMR(CDCl$_3$): δ1.35(s,3H); 1.92(br s,3H); 3.66(s,3H)); 4.05(ddd,1H); 5.36(m,2H); 5.50(dd,1H); 5.70(dt,1H); 6.08(d,1H); 6.50(dd,1H); 6.57(br d,1H).

EXAMPLE 8

(±)-methyl 19-fluoro-11α,16R-dihydroxy-16,20,20-trimethyl-9-oxoprosta-4Z,13E,17E, 19-tetraen-1-oate

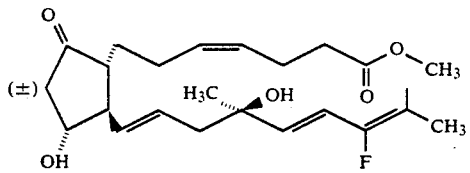

The reaction sequence shown in Reaction Scheme VII was followed to yield the above product. Into a reaction flask was added 25 gm (135 mmol) of bromofluoroethylacetate, 29.2 gm (176 mmol) of triethyl phosphite and the resultant mixture heated to about 150° C. under nitrogen. Ethyl bromide was distilled off and condensed as the reaction proceeded. After 3½ hours the reaction was cooled and the reaction mixture distilled under high vacuum and the fraction collected boiling at 105°–110° C. There was obtained 26.78 gm of the fluoromethylphosphonate. Into a reaction vessel containing 50 ml of dry THF at −8° C. was added 2.13 gm (21 mmol) of diisopropylamine and a solution of 8 ml (20 mmol) of n-butyllithium in hexane. After 30 minutes, 5.08 gm of the above phosphonate was added dropwise with stirring and the reaction mixture was stirred at room temperature overnight. Distilled acetone (2.94 ml) was added at room temperature to the Witting salt and a rapid temperature rise (from 25°–40° C.) was observed. The mixture was cooled to 3° C. and the remaining acetone added. The reaction mixture was stirred for 2 hours, poured into a cold mixture of dilute sodium chloride and 0.5 N HCl and shaken with ether (100 ml). The organic layer was separated, washed with cold sodium bicarbonate solution, saturated sodium chloride solution and dried over magnesium sulfate. Following filtration, the excess solvent was distilled off yielding 2.02 gm of the ethyl 2-fluoro-3- methyl-but-2-en-oate. The ester (0.438 gm, 3 mmol) was dissolved in THF and cooled to −5 to −10° C. To the mixture was added lithium aluminum hydride (2.25 ml, 2.25 mmol) slowly with stirring. After the addition, the reaction was held at room temperature for about 30 minutes. The reaction mixture was poured into cold saturated ammonium chloride solution and extracted once with diethyl ether and acidified with 2N HCl. The mixture was extracted with diethyl ether and washed with saturated sodium chloride and dried over magnesium sulfate. The solvent was distilled off at atmospheric pressure yielding the 2-fluorobutenol. The butenol was reacted in the same manner as discussed in Example 7 using 4.17 ml of DMSO, 2.5 ml of oxalyl chloride, 16.7 ml of triethylamine, 300 ml of dichloromethane and 10.0 gm of 1-triphenylphosphoranylidene-2-propanone. The reaction yielded 2.73 gm of the 6-methyl-5-fluoro-hept-3,5-diene-2-one having a boiling point of 55°–56° C. The ketone was reacted through a Grignard reaction in the method described in Example 7 using 3.35 gm (23.6 mmol) of the heptadienone, 3.54 gm (29.7 mmol) of propargyl bromide, 0.77 gm (31.9 mmol) of magnesium and 50 ml of THF. The Grignard step was complete after approximately 30 minutes to yield after workup 5.28 gm of a yellow oil which was chromatographed yielding 2.66 gm of the nonyne. The nonyne was reacted in a manner similar to that of Example 7. In a flask was added 1.27 gm of 7-fluoro-4,7-dimethyl-4-hydroxy-non-5,7-diene-1-yne (7.0 mmol) tributyltin hydride (3.06 gm, 10.5 mmol) and a trace of AIBN. The reagents were stirred under argon. After 4 hours of irradiation with a sunlamp at ambient temperature, the reaction mixture was purified by chromatography yielding 1.8 gm of the vinyl stannane product. The 1.8 gm of the 4-hydroxy-7-fluoro-4,8-dimethyl-1-trans-stannyl-1,5,7-octatriene (3.8 mmol) was protected with a trimethylsilyl group in the manner described in Example 7 using 0.60 ml (52 mg, 4.76 mmol) of trimethylchlorosilane, 0.41 gm imidazole (6 mmol) and 6 ml of DMF yielding 1.87 gm of the protected product. The trimethylsilyl vinyl stannane was reacted with n-butyllithium and pentynyl copper followed by the protected cyclopentenone to provide the protected prostaglandin product using the following quantities of reagents: 0.935 gm (1.7 mmol) of the vinylstannane; 0.68 ml (1.7 mmol) of n-butyllithium; 4 ml of THF; 0.25 gm of pentynyl copper (1.9 mmol); 0.64 gm of HMPT; 10 ml of ether; and 0.352 gm (1.0 mmol) of the triethylsilyl protected cyclopentenone. The resultant reaction workup provided 1.4 gm of a clear oil. Following chromatography, 0.31 gm of the prostaglandin product was obtained and this product was deprotected in a solution of 18 ml of acetone/water (5 to 1) containing approximately 15 mg of pyridine p-toluenesulfonate. The product of the above formula was obtained.

$^1$H NMR(CDCl$_3$): δ1.36(s,3H); 1.72(d,6H); 3.66(s,3H); 5.36(m,2H); 4.05(ddd,1H); 5.55(dd,1H); 5.75(dt,1H); 6.25(dd,1H); 5.92(dd,1H).

EXAMPLE 9

(±)-methyl 20,20-dichloro-11α,16R-dihydroxy-16-methyl-9-oxo-prosta-4Z,13E,17E,19-tetraen-1-oate

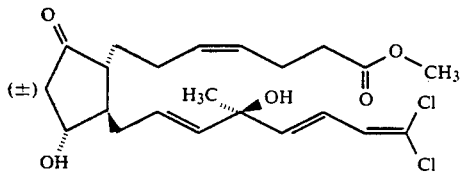

This 20-dichloro prostaglandin product was prepared following the sequence shown in Reaction Scheme VIII. Into a 500 ml three neck round bottom flask fitted with an argon inlet tube, addition funnel and thermometer probe was added 10.8 gm (40 mmol) of triethylsilyl protected hydroxy ester (prepared as discussed in Collins et al., *J. Med. Chem.*, in press 1992) (preparation also shown in J. Mayrarque et. al., *Bull. Chem. Soc. Fr.*, 1984, 11–129) 125 ml of toluene. The reaction mixture was cooled to −78° C. From the addition funnel at −78° C. was added 80 ml of 1.0 molar DIBAL (80 mmol, 2.0 eq) in toluene. The reaction mixture was stirred for 1 hour following completion of the addition. The reaction was quenched with 7.04 gm (0.16 mol) acetaldehyde in 50 ml toluene via dropwise addition from the addition funnel at −78° C. The reaction mixture was stirred for 1 hour. To the mixture was added 50 ml of an aqueous sodium sulfate solution at −78° C. and 200 ml of ether. The mixture was allowed to warm to 0° C. To the mixture was added 250 ml of 3N HCl and the layers separated. The acid layer was extracted once with 100 ml of ether. The organic layers were combined and stirred with 200 ml of 3N HCl for 15 minutes. The layers were separated and the ether layer washed sequentially with dilute sodium bicarbonate solution, water, followed by brine and dried over magnesium sulfate. The ether was stripped off, yielding 16.9 gm of the aldehyde (Shown in Reaction Scheme VIII). The residue was dissolved in 250 ml toluene, treated with 27.9 g of (carboethoxy)triphenylphosphorane and the reaction mixture refluxed overnight. The toluene was removed by evaporation and the residue slurried in hexane and filtered of solids. The hexane was stripped, yielding an oil which was slurried with hexane, then stripped, yielding 10.84 gm of the unsaturated ester as a crude yellow oil.

A solution of 7.74 g (26.1 mmol) of the above crude ester in 250 ml of methylene chloride (CH$_2$Cl$_2$) was cooled to −78° C. and treated dropwise with 57.4 ml of 1.0 M solution of DIBAL in CH$_2$Cl$_2$ (57.4 mmol). The reaction mixture was quenched with 100 ml of saturated sodium potassium tartrate solution, and poured into a mixture of ether and additional tartrate solution. The organic layer was separated, washed with brine, dried over magnesium sulfate, filtered, concentrated and redi- luted with more CH$_2$Cl$_2$. This solution was added slowly to a solution of 3.64 gm of oxalyl chloride, at 4.89 gm of DMSO (Swern conditions) at −78° C. After the addition was complete, the reaction mixture was warmed to −35° C. for 15 minutes and quenched by addition of 13.15 g of triethylamine. The reaction mixture was diluted with diethyl ether, the organic layer washed three times with 1N HCl, then water, dried over magnesium sulfate, stripped of solvent and the residue chromatographed to give 4.06 gm of unsaturated aldehyde.

In a 10 ml single neck round bottom flask fitted with a stirring bar, argon inlet tub,, was added 505 mg of the unsaturated aldehyde, 4 ml of dry CH$_3$CN; 1.57 gm (6 mmol) of triphenylphosphine cooled to 0° C.; and 594 mg (3 mmol) of bromotrichloromethane. The reaction mixture was stirred for 1 hour. The mixture was poured into a mixture of 50 ml ether and 50 ml water. The ether layer was washed twice with water, once with brine and dried over magnesium sulfate. After solvent removal the crude oil was purified on silica gel (hexane) to give 581 mg of a light yellow liquid of the dichloro product shown as compound 4 from reaction Scheme VIII.

In a three neck 25 ml round bottom flask fitted with a stirring bar, argon inlet tube, a digital thermometer, was added 575 mg (1.80 mmol) of the dichloro product in 5 ml THF. To the mixture was added 516 mg (2.0 mmol) of zirconocene chloride with stirring for 30 minutes at room temperature. The reaction mixture was cooled to −78° C. and 2.25 ml of 1.6 molar n-butyllithium added (3.6 mmol) and stirred for 1 hour at −78° C. To the reaction mixture was added 161 mg (1.8 mmol) of CuCN at −78° C. The reaction mixture was warmed to −50° C. and was stirred for a total of 30 minutes. To the reaction mixture was added 1.33 ml of 1.39 molar methyllithium (1.85 mmol) in cumene at −78° C. dropwise with stirring for 1 hour. To the reaction mixture was added by cannulation at −78° C., 353 mg (1.0 mmol) of the cyclopentenone in 3.5 ml THF. The reaction mixture was stirred for 1 hour at −78° C. The crude prostaglandin product (1.33 gm of yellow oil) was obtained by workup as described in Examples 7 and 8. Chromatographic purification provided 208 mg of protected prostaglandin. Deprotection was carried out by treatment with 20 ml of a 9 to 1 mixture of acetone and water containing 1 mg PPTS per ml. After 48 hours at room temperature the acetone was stripped in vacuo and the residue was taken up in a mixture of 100 ml ether and 10 ml of water. The layers were separated and the ether layer washed once with 20 ml of sodium bicarbonate solution, once with brine and dried over anhydrous magnesium sulfate. The mixture was filtered and stripped of solvent to yield 347 mg of residue containing the prostaglandin product. The mixture was purified by chromatography on a silica gel column using 70% ethyl acetate/hexane. Recovered were 28 mg of the above product.

EXAMPLE 10 methyl 16R-(fluoromethyl)-11α,16-dihydroxy-20,20-dimethyl-9-oxoprosta-4Z,13E,17E,19-tetraen-1-oate

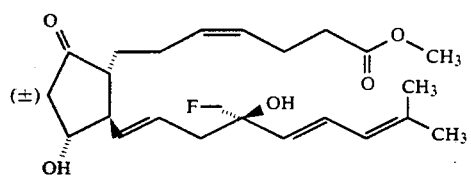

The 16-fluoromethyl prostaglandin derivative made herein was made following the reaction sequence shown in Scheme II and Scheme I. The fluoromethyl ketone was prepared by treatment of 3-methyl-2-butenal with 1-(fluoroacetyl)-methylene-triphenylphosphorane. The further synthesis was performed in the manner set forth in Example 1 and yielded 50 mg of the above identified 16-fluoromethyl product.

Analysis:

$^1$H NMR (CDCl$_3$): δ3.67 s(OCH$_3$); 4.28d, J=47.5 Hz (CH$_2$F); 5.53d, J=15 Hz (C-17H); 6.58dd, J=15, 11 Hz (C-18H); 5.83d, J=11 Hz (C-19H); 1.77s (C-20CH$_3$); 1.79 s (C-20CH$_3$);

$^{13}$C NMR: δ51.6 (OCH$_3$); 173.7 (C-1); 214.8 (C-9); 71.8 (C-11); 88.0 (CH$_2$F, J$_{CF}$=178 Hz); 74.1 (C-16, J$_{CCF}$=19 Hz); 18.4 (C-20CH$_3$); 26.0 (C-20CH$_3$).

EXAMPLE 11

Comparison of Acid Stability of Compound of Example 1 with its parent non-fluorinated analog.

Each compound (4 mg) was separately dissolved in 0.4 ml of a 3:1:1 solution of acetic acid:THF:water and kept at room temperature. Relative decomposition was assessed by thin layer chromatography analysis of aliquots withdrawn at 30 minutes, 1, 2, 4 and 6 hours. The results show that the non-fluorinated parent undergoes epimerization of the 16-hydroxyl group, allylic rearrangement to form the 20-hydroxy compound, and dehydration of the hydroxyl to give the tetraene at all time points with substantial conversion to the decomposition products at 6 hours. In contrast, virtually no decomposition products were observed with the compound of Example 1 at any time point.

A similar experiment performed in THF/0.1 N HCl and analyzed by HPLC showed the same results.

The following Table 1 provides the results of testing compounds of the invention herein showing the activity of the compounds when evaluated in the:

(1) Ethanol induced gastric lesion assay in rats;
(2) Gastric acid secretion assay in dogs; and
(3) Diarrheal assay in rats.

TABLE 1

| Compound Example # | Ethanol-Induced Gastric Lesion *MED μg/kg | Gastric Antisecretory (Dog) ED$_{50}$ μg/kg | Diarrhea Rat ED$_{50}$ μ/kg |
|---|---|---|---|
| Unfluorinated analog of Ex 1 | 1.0 | 0.02 | >3160 |
| 1 | 1.0 | 0.03 | >3160 |
| 2 | 1.0 | 0.02 | >3160 |
| 3 | 10 | >1.0 | >3160 |
| 4 | 100 | >0.1 | >3160 |
| 5 | 10 | >0.1 | N.D |
| 6 | I 100 | 84% inhibition at 0.3 | N.D |
| 7 | 50. | 74% inhibition at 0.3 | >3160 |
| 8 | 1.0 | 0.05 | N.D |
| 9 | 2.5 | 0.03 | 1000 |
| 10 | 25 | <0.3 | >3160 |

*MED = Minimal effective dose
N.D = Not Determined

I claim:

1. A compound of the formula

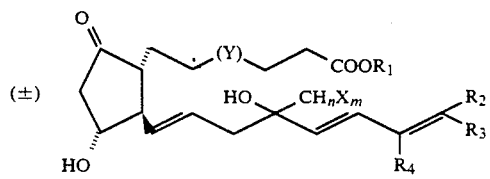

or a pharmaceutically acceptable salt thereof, wherein:

Y is —CH=CH— or —CH$_2$—CH$_2$—;

R$_1$ is H or a lower alkyl of 1 to 6 carbons;

n is an integer from 0 to 3;

m is an integer from 0 to 3 and n+m=3;

X is Cl or F provided that when X is Cl, n is 2 and m is 1;

R$_2$ and R$_3$ are independently H, lower alkyl from 1 to 6 carbons, Cl, —CH$_2$Cl, —Ch$_2$F, —CHCl$_2$, —CHF$_2$, —CCl$_3$, —CF$_3$ or taken together form a cycloalkyl of 3 to 6 carbons;

R$_4$ is H, lower alkyl from 1 to 6 carbons, Cl, F or taken together with R$_3$ forms a cycloalkenyl of 4 to 6 carbons; and provided that at least one of —CH$_n$X$_m$, R$_2$, R$_3$ and R$_4$ includes Cl or F.

2. A compound of the formula

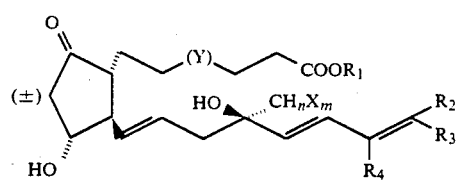

II or a pharmaceutically acceptable salt thereof, wherein:

Y is —CH=CH— or —CH$_2$CH$_2$—;

R$_1$ is H or lower alkyl of 1 to 6 carbons;

n is an integer from 0 to 3;

m is an integer from 0 to 3 and n+m=3;

X is Cl or F provided that n is 2 and m is 1 when X is Cl;

R$_2$ and R$_3$ are independently H, lower alkyl from 1 to 6 carbons, —CF$_3$, Cl or taken together form a cycloalkyl of 3 to 6 carbons;

R$_4$ is H, lower alkyl from 1 to 6 carbons, F or taken together with R$_3$ forms a cycloalkenyl of 4 to 6 carbons; and provided that at least one of —CH$_n$X$_m$, R$_2$, R$_3$ and R$_4$ includes Cl or F.

3. A compound as recited in claim 2 of the formula

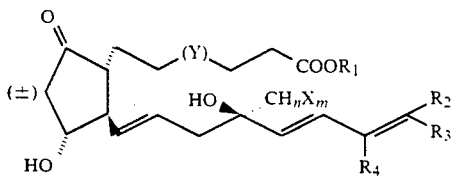

or a pharmaceutically acceptable salt thereof.

4. A compound as recited in claim 3 wherein Y is —CH=CH—.

5. A compound as recited in claim 4 wherein $R_3$ and $R_4$ are taken together to form a cyclopentene ring.

6. A compound as recited in claim 5 wherein X is F.

7. A compound as recited in claim 6 wherein m is 1 and n is 2.

8. A compound as recited in claim 5 wherein m is 2 and n is 1.

9. A compound as recited in claim 6 wherein m is 3 and n is 0.

10. A compound as recited in claim 5 wherein X is Cl.

11. A compound as recited in claim 4 wherein $R_3$ is —$CF_3$.

12. A compound as recited in claim 11 wherein $R_2$ is H.

13. A compound as recited in claim 11 wherein $R_2$ is methyl.

14. A compound as recited in claim 4 wherein $R_4$ is F.

15. A compound as recited in claim 14 wherein $R_2$ and $R_3$ are methyl.

16. A compound as recited in claim 4 wherein $R_2$ is Cl.

17. A compound as recited in claim 16 wherein $R_3$ is Cl.

18. A compound as recited in claim 4 wherein X is F and $R_2$ and $R_3$ are methyl.

19. A compound as recited in claim 3 wherein Y is —$CH_2$—$CH_2$—.

20. A compound as recited in claim 19 wherein $R_3$ and $R_4$ are taken together to form a cyclopentene ring.

21. A compound as recited in claim 19 wherein $R_3$ is —$CF_3$.

22. A compound as recited in claim 19 wherein $R_4$ is F.

23. A compound as recited in claim 19 wherein $R_2$ and $R_3$ are methyl.

24. A compound as recited in claim 1 which is methyl 7-[2β-[6-(1-cyclopenten-1-yl)-4R-(fluoromethyl)-4-hydroxy-1E,5E-hexadienyl]-3α-hydroxy-5-oxo-1R,1α-cyclopentyl]-4Z-heptenoate.

* * * * *

UNITED STATES PATENT AND TRADEMARK OFFICE
CERTIFICATE OF CORRECTION

PATENT NO. : 5,177,251          Page 1 of 3
DATED     : January 5, 1993
INVENTOR(S) : Collins, et al.

It is certified that error appears in the above-identified patent and that said Letters Patent is hereby corrected as shown below:

Abstract on cover page, line 13, reading "-CHCl$_2$, -CCl$_3$," should read -- -CHCl$_2$, CHF$_2$, -CCl$_3$, -CF$_3$--.

Column 9, line 18, reading "intrapritoneally," should read -- intraperitoneally, --.

Column 10, line 28, reading "rang ®" should read -- range --.

Column 10, line 48, reading "-oxo-lo-" should read -- -oxo-1α- --.

Column 11, line 56, reading "solution" should read -- solution. --.

Column 12, line 18, reading "hexane" should read -- hexane. --.

Column 14, line 65, reading "J = 15.18Hz" should read -- J = 15.8Hz --.

Column 19, line 12, reading "With" should read -- with --.

Column 21, line 52, represented by the formula reading

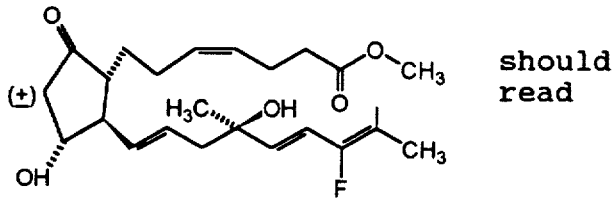 should read 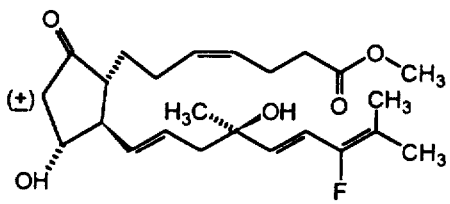

UNITED STATES PATENT AND TRADEMARK OFFICE
CERTIFICATE OF CORRECTION

PATENT NO. : 5,177,251

DATED : January 5, 1993

INVENTOR(S) : Collins, et al.

It is certified that error appears in the above-identified patent and that said Letters Patent is hereby corrected as shown below:

Column 22, line 10, reading "Witting" should read -- Wittig --.

Column 23, line 9, reading "(dd, IH);" should read -- (dd, 1H); --.

Column 23, line 17, represented by the formula reading

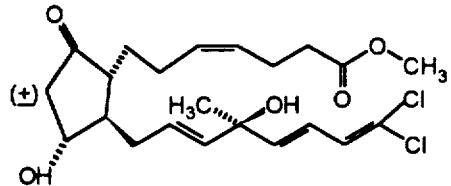 should read 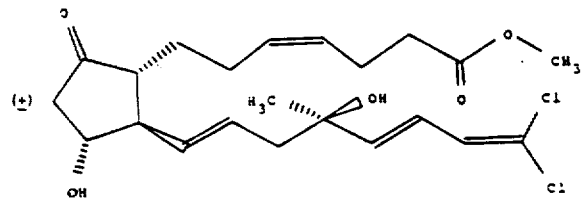

Column 24, line 15, reading "tub,," should read -- tube, --.

Column 26, line 35, reading "-Ch$_2$F," should read -- -CH$_2$F, --.

UNITED STATES PATENT AND TRADEMARK OFFICE
CERTIFICATE OF CORRECTION

PATENT NO. : 5,177,251

DATED : January 5, 1993

INVENTOR(S) : Collins, et al.

It is certified that error appears in the above-identified patent and that said Letters Patent is hereby corrected as shown below:

Column 26, line 54, reading "$-CH_2CH_2-;$" should read -- $-CH_2-CH_2-;$ --.

Signed and Sealed this

Third Day of May, 1994

Attest:

BRUCE LEHMAN

Attesting Officer

Commissioner of Patents and Trademarks